United States Patent
Gjerde et al.

(10) Patent No.: US 6,461,819 B1
(45) Date of Patent: Oct. 8, 2002

(54) ANALYSIS OF NICKED DNA BY MATCHED ION POLYNUCLEOTIDE CHROMATOGRAPHY UNDER DENATURING CONDITIONS

(75) Inventors: Douglas T. Gjerde, Saratoga; Paul D. Taylor, Gilroy, both of CA (US)

(73) Assignee: Transgenomic, Inc., San Jose, CA (US)

( * ) Notice: Subject to any disclaimer, the term of this patent is extended or adjusted under 35 U.S.C. 154(b) by 57 days.

(21) Appl. No.: 09/643,120

(22) Filed: Aug. 21, 2000

Related U.S. Application Data (63) Continuation of application No. 09/172,920, filed on Oct. 14, 1998, now Pat. No. 6,187,539, which is a continuation-in-part of application No. 09/136,084, filed on Aug. 18, 1998, now Pat. No. 6,027,898.

(60) Provisional application No. 60/062,413, filed on Oct. 14, 1997, provisional application No. 60/062,412, filed on Oct. 14, 1997, and provisional application No. 60/103,313, filed on Oct. 6, 1998.

(51) Int. Cl.[7] .............................. C12Q 1/68; G01N 1/00; G01N 15/00
(52) U.S. Cl. ............................ 435/6; 422/50; 422/68.1
(58) Field of Search .................................. 435/6; 422/50, 422/68.1

(56) References Cited

U.S. PATENT DOCUMENTS

| | | |
|---|---|---|
| 4,395,486 A | 7/1983 | Wilson et al. ............... 435/6 |
| 4,656,127 A | 4/1987 | Mundy ......................... 435/6 |
| 4,683,202 A | 7/1987 | Mullis ......................... 435/91 |
| 5,175,273 A | 12/1992 | Bischofberger et al. ..... 536/27 |
| 5,217,863 A | 6/1993 | Cotton et al. ............... 435/6 |
| 5,376,526 A | 12/1994 | Brown et al. ............... 435/6 |
| 5,459,039 A | 10/1995 | Modrich et al. ............. 435/6 |
| 5,585,236 A | 12/1996 | Bonn et al. .................. 435/5 |
| 5,589,329 A | 12/1996 | Winkler et al. ............. 435/5 |
| 5,698,400 A | 12/1997 | Cotton et al. ............... 435/6 |
| 5,763,178 A | 6/1998 | Chirikjian et al. .......... 435/6 |
| 5,869,245 A | 2/1999 | Yeung ........................ 435/6 |

FOREIGN PATENT DOCUMENTS

| | | | |
|---|---|---|---|
| WO | 95/29258 | 11/1995 | ............ C12Q/1/68 |
| WO | 97/09422 | 3/1997 | ............ C12N/9/22 |
| WO | WO97/21837 | 7/1997 | |

OTHER PUBLICATIONS

Brow et al, Cleavase Gragment Length Polymorphism Analysis for Mutation Scanning, Biomedical Products (Sep. 1997).

Chan et al. Sequence Specificity and Biochemical Characterization of He Rusa Holliday Junction Reolvase of Exchericihia coli, The Journal of Biological Chemistry, vol. 272, No.23, Jun. 6, 1997, pp. 14873–14882.

(List continued on next page.)

*Primary Examiner*—Ardin H. Marschel
(74) *Attorney, Agent, or Firm*—John F. Brady (57) ABSTRACT

The present invention provides a method for calibrating a MIPC column wherein the calibration relates to the determination of the organic solvent component in the mobile phase required to elute dsDNA fragments of different base pair lengths at specific retention times. Since a MIPC column affords highly reproducible separations, once calibrated, the base pair length of unknown dsDNA fragments can be determined by comparing their retention times to those obtained on a standard calibration chromatogram. The standard calibration chromatogram is obtained by chromatographing a standard dsDNA ladder containing fragments of known base pair length. In addition, a method is provided to determine the presence of nicks in dsDNA using MIPC under fully denaturing conditions, e.g., 80° C. In one embodiment, this method is applied to the detection of mutations in dsDNA.

4 Claims, 4 Drawing Sheets

OTHER PUBLICATIONS

Cotton et al, Reactivity of Cytosine ANS Thymine in Single–Base–Pair Mismatches with Hydrozylamine an Osmium Tetroxide and Its Application to the Stury of Mutations, Proc. Natl. Acad. Sci. USA, 85: 4397–4401 (Jun. 1988).

Cotton et al, Slowly by Surely Towards Better Scanning for Mutations, TIG, vol. 13 No. 2: 43–46 (Feb. 1997).

Ellis et al, Chemical Cleavage of Mismatch: A New Look at an Established Method, Human Mutation, 11: 345–353 (1998).

Gidney et al. 1.10–Phenanthroline and 2,2–Bipyridyl Complexes of Rhodium (iii), JCS Dalton (1972) pp. 2621–2628.

Giraud–Panis et al. T4 Endonuclese VII, Importance of a Histidine–Asparate Cluster within the Zinc–Binding Domain, The Journal of Biological Chemistry, 271, pp. 33148–33155, 1996.

Holmlin et al., RU(PHEN)2DPPZ2+ Luminescence: Dependence on DNA Sequences and Groove–Binding Agents, Inorg. Chem. (1998) 37: 29–34.

http://journals.wiley.co . . . 9–7794/abs/v7n3p256.html (Jun. 26, 1998) Citing: Hansen et al, Human Mutation, vol. 7 No. 3: 256–263 (1996).

http://wsrv.clas.virginia.edu/~rjh9u/restdna1.html Restriction Enzyme Cleavage of DNA, (Jun. 26, 1998).

http://www.jbc.org/cgi/c    .    .    .    =QID_NOT_SET&FIRSTINDEX= (Sep. 21, 1998) Citing: J. Biol. Chem., vol. 273 Iss 15: 9202–9207 (Apr. 1998).

http://www.jbc.org/cgi/c    .    .    .    =QID_NOT_SET&FIRSTINDEX= (Sep. 21, 1998) Citing: Taylor et al, Strand Specificity of Nicking of DNA and CHI Sites by RECBCD Enzyme, JBC Online, vol. 270 No. 41: 24459–24467 (Oct. 1995).

Huber et al, High–Resolution Liquid Chromatography of Oligonucleotides on Nonporous Alkylated Styrene–Divinylbenzene Copolymers, Analytical Biochemistry, 212: 351–358 (1993).

Jackson et al, Recognition of DNA Base Mismatches by a Phodium Intercalator. J. Am. Chem. Soc., vol. 119 No. 32: 12986–12987 (1997).

Mashal et al, Detection of Muations by Cleavage of DNA Heteroduplexes with Bacteriophage Resolvases, Nature Genetics, 9: 177–183 (Feb. 1995).

Mashal et al, Practical Methods of Mutation Detection, Genetics & Development, 6. 275–280 (1998).

Molecular Cloning, A Laboratory Manual, 2nd ed, Cold Spring Harbor Laboratory Press, 1989, pp. 13.2–13.10.

Myers et al, Detection of Single Base Changes in DNA: Ribonuclease Cleavage and Denaturing Gradient Gel Electrophoresis, Genomic Analysis: A Practical Approach, PRL Press, K. Davies, ed. (1988).

Myers et al. Genomic Analysis: A Practical Approach, IRL Press, K. Davis, ed. (1988) pp. 95–138.

Oleykowski et al, Mutation Detection Using a Novel Plant Endonuclease, Nucleic Acids Research, vol. 26 No. 20: 4597–4602 (1998).

Rowley et al., Ultrarapid Mutation Detection by Multiplex, Solid–Phase Chemical Cleavage, Genomics, 30, 574–582, 1995.

Shida et al. Anlysis of Substrate Specificity of the RUVC Holliday Junction Resolvase with Syntheic Holliday Junctions, The Journal of Biological Chemistry, vol. 271, No. 42, Oct. 18, 1996, pp. 26105–26109.

Smith et al. Mutation Detection with MUTH, MUTL, and MUTS Mismatch Repair Proteins, Proc. Natl. Acad. Sci. USA, Genetics, 93, pp. 4374–4379, Apr. 1996.

Stemp et al, Oxidation of Guanine in DNA by Ru(phen)2(dppz)3+ Using the Flash–Quench Technique, J. Am. Chem. Soc., vol. 119 No. 12: 2921–2923 (1997).

Taylor, Graham R., Laboratory Methods for the Detection of Mutations and Polymorphisms in DNA, Ch. 9, 18–22, CRC Press. Boca Raton, New York (1997).

Wagner et al. Mutation Detection Using Immobilized Mismatch Binding Protein (MUTS), Nucleic Acids Research, 25, 19, pp. 3944–3948, 1995.

Xu et al. Determining the Site and Nature of DNA Mutations with the Cloned MUTY Mismatch Repair Enzyme, Carcinogenesis, vol. 17, No. 2, pp. 321–326, 1996.

Youil et al, Screening for Mutations by Enzyme Mismatch Cleavage with T4 Endomuclease VII, Proc. Natl. Acad. Sci. USA, 92: 87–91 (1995).

Sitlani et al DNA Photocleavge by Piienanthrenequinon Diimine Complexes of Phodium (III): Shape–Selective Recognition and Reaction. J. Am. Chem. Soc. 1992. 114, 2303–2312.

Fig. 5   TIME (MINUTES) Chromatograms are offset by 5 millivolts

ANALYSIS OF NICKED DNA BY MATCHED ION POLYNUCLEOTIDE CHROMATOGRAPHY UNDER DENATURING CONDITIONS

CROSS REFERENCE TO RELATED CO-PENDING APPLICATIONS

This is a continuation of U.S. patent application Ser. No. 09/172,920 filed Oct. 14, 1998 (now U.S. Pat. No. 6,187,539) which is a continuation-in-part of U.S. patent application Ser. No. 09/136,084 filed Aug. 18, 1998 (now U.S. Pat. No. 6,027,898) and claims the benefit of provisional applications 60/103,313 filed Oct. 6, 1998, Ser. No. 60/062,413 and Ser. No. 60/062,412 both filed Oct. 14, 1997.

FIELD OF THE INVENTION

The present invention concerns an improved method for the analysis and detection of nicks in double stranded DNA.

BACKGROUND OF THE INVENTION

The term "nick" is defined herein to mean a double stranded (ds) DNA fragment wherein one of the strands is contiguous and the complimentary strand contains at least one break, wherein two adjacent bases are not covalently linked. "Nicks" in DNA fragments occur for a variety of reasons. For example, when long DNA fragments are constructed by enzymatic ligation of shorter strands, some fragments may not be completely ligated. Important and widely used products of DNA ligation comprise commercially produced DNA sequencing "ladders" (BioRad, Inc., Richmond, Calif.; Life Technologies, Inc., Germantown, Md.). DNA "ladders" are mixtures of DNA fragments, wherein the fragments comprise a defined range of base pair lengths and the fragments in the ladder differ by a constant base pair increment. For example, a 100 base pair (100 bp) ladder contains DNA fragments which differ by 100 bp increments over a range of 100 bp to 3,000 bp, i.e., 100 bp, 200 bp, 300 pb, 400 bp . . . 3,000 bp. Such DNA ladders are used as base pair length standards to calibrate electrophoresis gels. The accuracy of such ladders is of critical importance, since defective or impure ladders may lead to incorrect interpretation of sample results when compared to the standard base pair ladders. However, while a ladder containing nicks might be usable as a standard for gel electrophoresis, Applicants have found that such a ladder is not suitable for use as a standard using the more accurate and sensitive separation methods described herein.

Nicks are also formed when an enzyme which recognizes a base pair mismatch (mutation) in a heteroduplex, binds within the vicinity of a mutation and cleaves one strand of the DNA duplex which contains a non-complimentary base while leaving the other strand intact. Many such enzymes are known in the art and they are the basis of one form of mutation detection. For a comprehensive description of this subject see U.S. Pat. No. 5,763,178 to Chirikjian (1998). This reference and the references contained therein are incorporated in their entireties herein.

A nick in dsDNA cannot be detected by either gel or capillary electrophoresis of native DNA directly. Nicked strands can be detected, however, using denaturing polyacrylamide gels (*Molecular Cloning*, 2$^{nd}$ Ed. Sambrook et al. eds. Cold Spring Harbor Laboratory Press, 1989, incorporated herein by reference). Gel electrophoresis can also separate and detect nicked double stranded fragments which have been tagged with fluorescent or radioactive probes. However, this approach is costly and very labor intensive in that it requires the preparation of DNA fragments tagged with expensive probes. Methods which depend on gel electrophoresis (GEP) for separation of DNA fragments are subject to inherent deficiencies. This separation method is difficult to implement, not always reproducible, not accurate, difficult to quantify, and routinely takes five hours or more to complete (not counting set up time).

Other limitations in using GEP are related to the development and interpretation of bands on gels. The bands are often curved rather than straight, their mobility and shape can change across the width of the gel and lanes and bands can mix with each other. The sources of such inaccuracies stem from the lack of uniformity and homogeneity of the gel bed, electroendosmosis, thermal gradient and diffusion effects, as well as host of other factors. Inaccuracies of this sort are well known in the GEP art and can lead to serious distortions and inaccuracies in the display of the separation results. In addition, the band display data obtained from GEP separations is not quantitative or accurate because of the uncertainties related to the shape and integrity of the bands. True quantitation of linear band array displays produced by GEP separations cannot be achieved, even when the linear band arrays are scanned with a detector and the resulting data is integrated, because the linear band arrays are scanned only across the center of the bands. Since the detector only sees a small portion of any given band and the bands are not uniform, the results produced by the scanning method are not accurate and can even be misleading.

DNA molecules are polymers comprising sub-units called deoxynucleotides. The four deoxynucleotides found in DNA comprise a common cyclic sugar, deoxyribose, which is covalently bonded to any of the four bases, adenine (a purine), guanine (a purine), cytosine (a pyrimidine), and thymine (a pyrimidine), hereinbelow referred to as A, G, C, and T respectively. A phosphate group links a 3'-hydroxyl of one deoxynucleotide with the 5'-hydroxyl of another deoxynucleotide to form a polymeric chain. In double stranded DNA, two strands are held together in a helical structure by hydrogen bonds between, what are called, complimentary bases. The complimentarity of bases is determined by their chemical structures. In double stranded DNA, each A pairs with a T and each G pairs with a C, i.e., a purine pairs with a pyrimidine. Ideally, DNA is replicated in exact copies by DNA polymerases during cell division in the human body or in other living organisms. DNA strands can also be replicated in vitro by means of the Polymerase Chain Reaction (PCR).

Sometimes, exact replication fails and an incorrect base pairing occurs, which after further replication of the new strand results in double stranded DNA offspring containing a heritable difference in the base sequence from that of the parent. Such heritable changes in base pair sequence are called mutations.

In the present invention, double stranded DNA is referred to as a duplex. When the base sequence of one strand is entirely complimentary to the base sequence of the other strand, the duplex is called a homoduplex. When a duplex contains at least one base pair which is not complimentary, the duplex is called a heteroduplex. A heteroduplex duplex is formed during DNA replication when an error is made by a DNA polymerase enzyme and a non-complimentary base is added to a polynucleotide chain being replicated. Further replications of a heteroduplex will, ideally, produce homoduplexes which are heterozygous, i.e., these homoduplexes will have a complimentary, but altered sequence compared to the original parent DNA strand. When the parent DNA has the sequence which predominates in a natural population it is generally called the "wild type."

Many different types of DNA mutations are known. Examples of DNA mutations include, but are not limited to, "point mutation" or "single base pair mutations" wherein an incorrect base pairing occurs. The most common point mutations comprise "transitions" wherein one purine or pyrimidine base is replaced for another and "transversions" wherein a purine is substituted for a pyrimidine (and visa versa). Point mutations also comprise mutations wherein a base is added or deleted from a DNA chain. Such "insertions" or "deletions" are also known as "frameshift mutations". Although they occur with less frequency than point mutations, larger mutations affecting multiple base pairs can also occur and may be important. A more detailed discussion of mutations can be found in U.S. Pat. No. 5,459,039 to Modrich (1995), and U.S. Patent No. 5,698,400 to Cotton (1997). These references and the references contained therein are incorporated in their entireties herein.

The sequence of base pairs in DNA codes for the production of proteins. In particular, a DNA sequence in the exon portion of a DNA chain codes for a corresponding amino acid sequence in a protein. Therefore, a mutation in a DNA sequence may result in an alteration in the amino acid sequence of a protein. Such an alteration in the amino acid sequence may be completely benign or may inactivate a protein or alter its function to be life threatening or fatal. On the other hand, mutations in an intron portion of a DNA chain would not be expected to have a biological effect since an intron section does not contain code for protein production. Nevertheless, mutation detection in an intron section may be important, for example, in a forensic investigation.

Detection of mutations is, therefore, of great interest and importance in diagnosing diseases, understanding the origins of disease and the development of potential treatments. Detection of mutations and identification of similarities or differences in DNA samples is also of critical importance in increasing the world food supply by developing diseases resistant and/or higher yielding crop strains, in forensic science, in the study of evolution and populations, and in scientific research in general (Guyer et al., *Proc. Natl. Acad. Sci. USA* 92:10841 (1995); Cotton, *TIG* 13:43 (1997)). These references and the references contained therein are incorporated in their entireties herein.

Alterations in a DNA sequence which are benign or have no negative consequences are sometimes called "polymorphisms". In the present invention, any alterations in the DNA sequence, whether they have negative consequences or not, are called "mutations". It is to be understood that the method of this invention has the capability to detect mutations regardless of biological effect or lack thereof. For the sake of simplicity, the term "mutation" will be used throughout to mean an alteration in the base sequence of a DNA strand compared to a reference strand. It is to be understood that in the context of this invention, the term "mutation" includes the term "polymorphism" or any other similar or equivalent term of art.

Analysis of DNA samples has historically been done using gel electrophoresis. Capillary electrophoresis has been used to separate and analyze mixtures of DNA. However, in addition to the problems cited herein above, these methods cannot distinguish point mutations from homoduplexes having the same base pair length.

In addition to the deficiencies of denaturing gel methods mentioned above, these techniques are not always reproducible or accurate since the preparation of a gel and running an analysis is highly variable from one operator to another.

Recently, an HPLC method was introduced to effectively separate mixtures of double stranded polynucleotides, in general and DNA, in particular, wherein the separations are based on base pair length (U.S. Pat. No. 5,585,236 to Bonn (1996); Huber, et al., *Chromatographia* 37:653 (1993); Huber, et al., *Anal. Biochem.* 212:351 (1993)). These references and the references contained therein are incorporated herein in their entireties. However, the reproducibility, accuracy, column life, and reliability of this method have not been adequately addressed. Aspects of DNA separation and mutation detection by HPLC which have been recognized and addressed by Applicants include the treatment of, and materials comprising chromatography system components, the treatment of, and materials comprising separation media, solvent pre-selection to minimize methods development time, optimum temperature pre-selection to effect partial denaturation of a heteroduplex during chromatography and optimization of the chromatographic separation for automated high throughput mutation detection screening assays. These factors are essential in order to achieve unambiguous, accurate and reproducible mutation detection results using HPLC. Applicants, through their own work, have gained an understanding of the unique mechanism involved in the liquid chromatographic separation of DNA and termed their separation method "Matched Ion Polynucleotide Chromatography" (MIPC). This understanding has allowed Applicants to address the aspects related to the HPLC separation of polynucleotides in general and DNA in particular which have heretofore been unknown in the art.

There exists a need for a reliable method of calibrating a MIPC column to determine the relationship between the mobile phase composition and the base pair length of eluted fragments.

There exists a need for an accurate and reproducible analytical method for detecting nicked DNA which is easy to implement. Such a method, which in addition, can be automated and provide high throughput sample screening with a minimum of operator attention, is also highly desirable.

SUMMARY OF THE INVENTION

In one aspect, the present invention provides a method for determining the presence of "nicks" in a dsDNA fragment. In a further aspect, the invention provides an accurate method for determining the presence of a site of mismatch in a dsDNA sample. In another aspect the invention provides a method of calibrating a MIPC column by developing a relationship between the mobile phase composition and the retention time of dsDNA fragments having different base pair lengths, wherein the base pair lengths are within a specified base pair length range, such as a DNA ladder.

In still a further aspect, the invention provides an improved analytical method for the detection of mutations in nucleic acids. Yet another aspect is to provide a method for mutation detection which is highly reproducible, accurate, easily implemented and which can be automated for use with high throughput mutation detection assays or other analyses which require screening a large number of samples.

In one aspect, the invention provides a method for calibrating a Matched Ion Polynucleotide Chromatography column including the following steps: (a) applying to the column a sample containing a mixture of double stranded DNA fragments of known base pair length; (b) eluting the fragments; (c) detecting the eluted fragments; and (d) identifying the solvent concentration in the mobile phase at which each DNA fragment in the mixture elutes, whereby a relationship is derived between the organic solvent concentration in the mobile phase required for eluting DNA fragments of different base pair length from the column as a function of base pair length. In one embodiment of the invention, the DNA mixture is a DNA ladder. The DNA ladder can be pre-treated with a ligase to seal any nicks. In another embodiment, the mixture is a restriction enzyme digest.

In another aspect, the present invention is a method for determining the presence of a nick in a fragment of double stranded DNA by the following steps: (a) applying the fragment to a Matched Ion Polynucleotide Chromatography column; (b) eluting the fragment under fully denaturing conditions; (c) detecting the single stranded DNA species eluted in step (b); and (d) quantifying the single stranded DNA species from step (c) wherein at least three single stranded DNA species are detected if said fragment has a nick. The preferred denaturing conditions in step (b) are sufficient to completely denature the fragment. Examples of these conditions include an elevated level of at least one of the following: temperature (e.g. 60–80° C.), urea concentration (e.g., about 5M), dimethylformamide concentration, organic solvent concentration, counterion concentration, and pH (e.g. pH 9–12).

In still another aspect, the invention is a method for determining the presence of nicked DNA in a sample of double stranded DNA fragments and includes the following steps: (a) applying a first aliquot of the sample to a Matched Ion Polynucleotide Chromatography column; (b) eluting the fragments in the first aliquot under non-denaturing conditions; (c) detecting the DNA species eluted in step (b); (d) determining the number of DNA species detected in step (c); (e) applying a second aliquot of the sample to a Matched Ion Polynucleotide Chromatography column; (f) eluting the fragments in the second aliquot under denaturing conditions; (g) detecting the DNA species eluted in step (f); (h) determining the number of DNA species detected in step (g); and (i) comparing the number in step (d) to the number in step (h) to determine whether or not the number in step (h) exceeds twice the number in step (d) whereby the presence of nicked DNA is indicated if the number in step (h) exceeds twice the number in step (d). The preferred denaturing conditions in step (f) are sufficient to completely denature the fragments. Examples of these conditions include an elevated level of at least one of the following: temperature (e.g. 60–80° C.), urea concentration (e.g., 5M), dimethylformamide concentration, organic solvent concentration, counterion concentration, and pH (e.g. pH 9–12).

In yet another aspect, the invention provides a method for analyzing a sample of double stranded DNA to determine the presence of a mutation in the sample. The method includes: (a) contacting the sample with a mutation site binding reagent under conditions which allow the reagent to nick a strand of the double stranded DNA at or near the site of a mutation; (b) applying a first aliquot of the product of step (a) to a Matched Ion Polynucleotide Chromatography column; (c) eluting the fragments in the first aliquot under non-denaturing conditions; (d) detecting the DNA species eluted in step (c); (e) determining the number of DNA species detected in step (d); (f) applying a second aliquot of the product of step (a) to a Matched Ion Polynucleotide Chromatography column; (g) eluting the fragments in from step (f) under denaturing conditions; (h) detecting the DNA species eluted in step (g); (i) determining the number of DNA species detected in step (h); and (j) comparing the number in step (e) to the number in step (i) to determine whether or not the number in step (i) exceeds twice the number in step (e) whereby the presence of nicked DNA is indicated if the number in step (i) exceeds twice the number in step (e). In a preferred embodiment, the sample of double stranded DNA is the product of a hybridization of a DNA sample suspected of containing a mutation with corresponding wild type DNA. In a preferred embodiment, the mutation site binding reagent is an enzyme. Examples of suitable enzymes include S1 nuclease, mung bean endoucleose, CEL 1, mismatch repair enzymes, MutY protein, MutS protein, MutH protein, MutL protein, cleavase, exonuclease III, and HINF1. In another embodiment of this aspect of the invention, the mutation site binding reagent is a non-proteinaceous chemical reagent. A preferred chemical agent is an organometallic DNA intercalator. A preferred intercalator contains rhodium or ruthenium. Examples of suitable intercalators include bis(2,2'-bipyridyl)chrysenequinone diimine rhodium(III), bis(2,2'-bipyridyl)chrysenequinone diimine rhodium(III), (2,2'-bipyridyl)-bis(phenanthrenequinone) diimine rhodium(III), (bis(phenanthroline)dipyridophenazine ruthenium(II), and bis(phenanthroline)dipyridophenazine ruthenium(III).

In still another aspect, the invention provides a chromatographic method for analyzing a sample of double stranded DNA to determine the presence of a mutation in said sample, the method including the steps of: (a) separating a first aliquot of the sample using Matched Ion Polynucleotide Chromatography to produce a first chromatogram comprising peaks or other shapes (e.g. bands) which represent separated components of the sample; (b) contacting another aliquot of said sample with a mutation site binding reagent under conditions which allow the reagent to nick a strand of DNA at or near the site of a base pair mismatch; (c) separating the product of step (b) by the chromatographic method of step (a) to produce a second chromatogram; and (d) comparing the chromatogram of step (c) to the chromatogram of step (a), wherein a change in the retention time or the number of peaks or other shapes in the chromatogram of step (c) indicates the presence of a mutation in the original sample. In one embodiment, the separation of step (a) is performed under non-denaturing conditions. In a preferred embodiment, the separation of step (a) is performed under denaturing conditions. Also in a preferred embodiment, the sample of double stranded DNA is the product of a hybridization of a DNA sample suspected of containing a mutation with corresponding wild type DNA. In a preferred embodiment, the mutation site binding reagent is an enzyme. Examples of suitable enzymes include S1 nuclease, mung bean endoucleose, CEL 1, mismatch repair enzymes, MutY protein, MutS protein, MutH protein, MutL protein, cleavase, exonuclease III, and HINF1. In another embodiment of this aspect of the invention, the mutation site binding reagent is a non-proteinaceous chemical reagent. A preferred chemical agent is an organometallic DNA intercalator. A preferred intercalator contains rhodium or ruthenium. Examples of suitable intercalators include bis(2,2'-bipyridyl)chrysenequinone diimine rhodium(III), bis(2,2'-bipyridyl)chrysenequinone diimine rhodium(III), (2,2'-bipyridyl)-bis(phenanthrenequinone) diimine rhodium(III), (bis(phenanthroline)dipyridophenazine ruthenium(II), and bis(phenanthroline)dipyridophenazine ruthenium(III).

BRIEF DESCRIPTION OF THE DRAWINGS

FIG. 5 is a series of MIPC chromatograms of un-nicked 100 bp DNA ladders and pUC18 DNA HaeIII restriction enzyme digests.

DETAILED DESCRIPTION OF THE INVENTION

In its most general form, the present invention relates to a novel method for the separation and detection of nicked DNA fragments in the presence of fully contiguous DNA duplexes using HPLC. More specifically, the invention relates to a novel method for detecting nicked DNA using Matched Ion Polynucleotide Chromatography (MIPC).

Ion Pairing Reverse Phase HPLC (IPRPHPLC) effectively separates mixtures of double stranded polynucleotides, in general and DNA, in particular, wherein the separations are based on base pair length (U.S. Pat. No. 5,585,236 to Bonn (1996)). IPRPHPLC is not limited by any of the deficiencies associated with gel based separation methods.

The term "Matched Ion Polynucleotide Chromatography" (MIPC) as used herein is defined as a process for separating single and double stranded polynucleotides using non-polar separation media, wherein the process uses a counter-ion agent, and an organic solvent to release the polynucleotides from the separation media. MIPC separations can be completed in less than 10 minutes, and frequently in less than 5 minutes. MIPC systems (WAVE™ DNA Fragment Analysis System, Transgenomic, Inc. San Jose, Calif.) are equipped with computer controlled ovens which enclose the columns and fluid areas.

MIPC uses unique non-polar separation media which include organic polymers, silica media having a non-polar surface comprising coated or covalently bound organic polymers or covalently bound alkyl and/or aryl groups, continuous monolith or rod columns comprising non-polar silica gel or organic polymer. The separation media used in MIPC can be porous or non-porous. A detailed description of the MIPC separation process, MIPC separation media, and MIPC systems is found in U.S. Pat. No. 5,772,889 (1998) to Gjerde and in co-pending U.S. patent applications Ser. No. 09/058,580 filed Apr. 10, 1998; U.S. Ser. No. 09/058,337 filed Apr. 10, 1998; U.S. Ser. No. 09/065,913 filed Apr. 24, 1998; U.S. Ser. No. 09/081,040 filed May 18,1998; U.S. Ser. No. 09/081,039 filed May 18, 1998; U.S. Ser. No. 09/080,547 filed May 18,1998; U.S. Ser. No. 09/129,105 filed Aug. 4, 1998; the U.S. provisional patent application identified by the Attorney Docket No. TRAN1-141 entitled "Non-polar Media for Polynucleotide Separations" filed Oct. 6, 1998. The entire contents of this patent and these applications are hereby incorporated by reference. MIPC systems and separation media are commercially available (Transgenomic, Inc. San Jose, Calif.). The entire MIPC analysis can be automated by means of a desk top computer and a sample auto-injector. Analytical data for each sample can be analyzed in real time, or collected and stored in a computer memory device for analysis at a later time.

Of critical importance in achieving good separations of DNA fragments is the need to maintain an environment wherein all the liquid contacting surfaces of the MIPC system are substantially free of multivalent cation contamination. The problems and solutions related to multivalent cation contamination were surprisingly discovered by Applicants and are described in detail in the U.S. patent and patent applications cited hereinabove. Therefore, MIPC systems comprise materials, which do not release multivalent cations, such as titanium, stainless steel, Fe(III), Cr(III), colloidal metal contaminants, or organic polymer. In addition, multivalent cation capture resin cartridges are placed in line between the mobile phase reservoir and the solvent pumps. Cation capture resin cartridges can also be installed at the top of the MIPC column packing to further ensure removal of multivalent cations which may be present in the sample.

Although nicks in DNA cannot be detected under non-denaturing conditions by gel based separation methods, they can be detected by MIPC. Despite the fact that MIPC separates DNA based on base pair length rather than base sequence, DNA fragments of the same base pair length can be separated if there is a significant alteration in the DNA structure. Thus, nicked DNA fragments separate from their un-nicked counterparts using MIPC.

Under non-denaturing conditions, the MIPC process separates DNA fragments in a sample by base pair length into separate populations of fragments having the same or closely related base pair length. The separated populations of fragments are detected, preferably using a uv absorbance detector. The output of the detector is obtained and displayed as a function of time and preferably consists of peaks or bands which represent the separate populations of fragments. Under partially or fully denaturing conditions, the relative polarity of the fragments influences the separation, with more polar fragments eluting earlier than less polar fragments.

One embodiment of the present invention concerns the calibration of MIPC columns using DNA ladders or restriction enzyme digests which produce an array of known base pair length fragments. MIPC separation media, unlike other separation media, furnishes highly reproducible separations from run to run and from day to day. Retention times are reproducible from run to run, or even from day to day. Therefore, DNA ladders or other standards can be used to calibrate MIPC columns for the retention times relative to base pair length.

DNA ladders are used extensively in the biotechnology as base pair length standards on electrophoresis gel slabs. Yet no methods have been reported to date for rapid and convenient analysis of the integrity of the fragments comprising DNA ladders. Since nicked fragments do not separate by non-denaturing GEP, the presence or absence of nicks was not an important issue. However, with the steadily increasing use of MIPC to separate DNA fragments for every purpose, the presence of nicked fragments in a DNA ladder can lead to ambiguous analytical and column calibration results.

Figure 1:
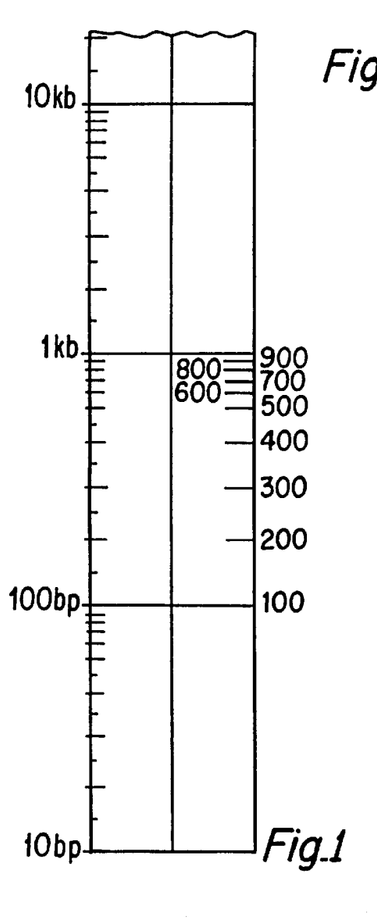
FIG. 1 is an electropherogram of a series of a DNA sequencing ladder.

In U.S. patent application Ser. No. 09/039,061 filed Mar. 13, 1998, Applicants describe a novel method for displaying bands from the polynucleotide fragments in a mixture separated my MIPC. The output can be made to resemble a "gel" and therefore more readily recognizable and interpretable. Thus, the use of DNA ladders as base pair standards for MIPC would be advantageous since these are already widely used and recognized in the gel electrophoresis art. However, in attempting to use DNA ladders as standards for MIPC, Applicants observed that a commercially available 100 bp DNA ladder (Catalogue No. 170-8206, BioRad, Inc. Richmond, Calif.) contains significant amounts of standard base pair fragments which are nicked as revealed by analysis using MIPC under non-denaturing conditions (about 50° C.). This was unexpected, since this standard produces homogenous bands in a GEP separation (FIG. 1). The presence of nicks is evident from FIG. 2, which shows the separation of the same 100 bp ladder shown in FIG. 1 except that the separation was effected by MIPC rather than GEP. The peak at just under 10 minutes retention time to the left of the 200 bp is a nicked 200 bp fragment. This conclusion was confirmed when ladder components separated by MIPC under non-denaturing conditions were isolated and re-chromatographed at 80° C. DNA duplexes are completely denatured into single strands at 80° C. Therefore, an un-nicked fragment would be expected to produce two single strands, represented as two peaks in the chromatogram. A nicked fragment would be expected to produce more than two fragments and, therefore, more than two peaks in the chromatogram.

Figure 3:
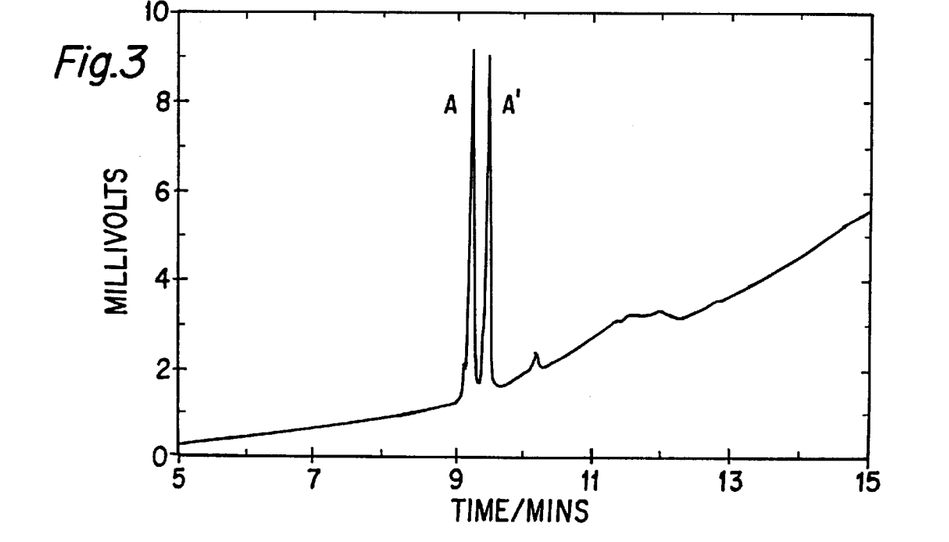
FIG. 3 is a MIPC chromatogram of an isolated 100 bp DNA duplex ladder fragment chromatographed under denaturing conditions.
Figure 4:
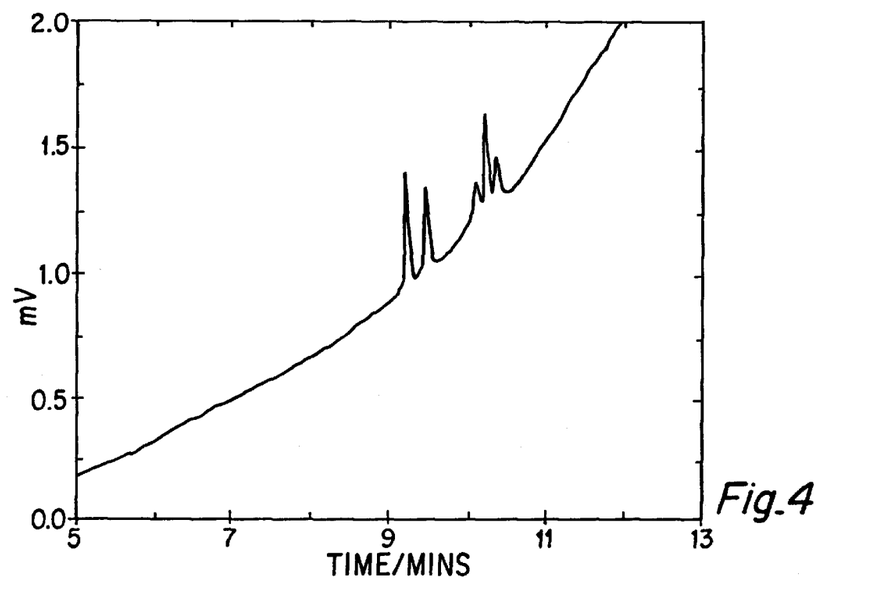
FIG. 4 is a chromatogram of an isolated 200 bp DNA fragment which contains one nick, chromatographed under denaturing conditions.
Figure 6:
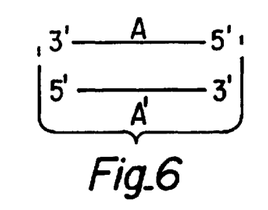
FIG. 6 is a schematic representation of a 100 bp DNA duplex.
Figure 7:
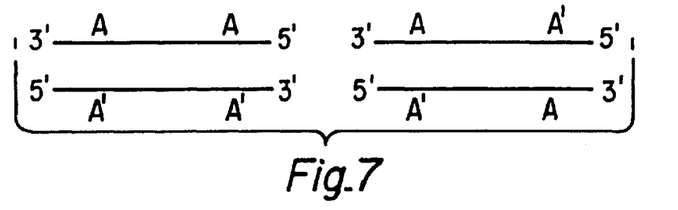
FIG. 7 shows a schematic representation of two 200 bp DNA duplexes formed by ligation of two 100 bp duplexes.
Figure 8:
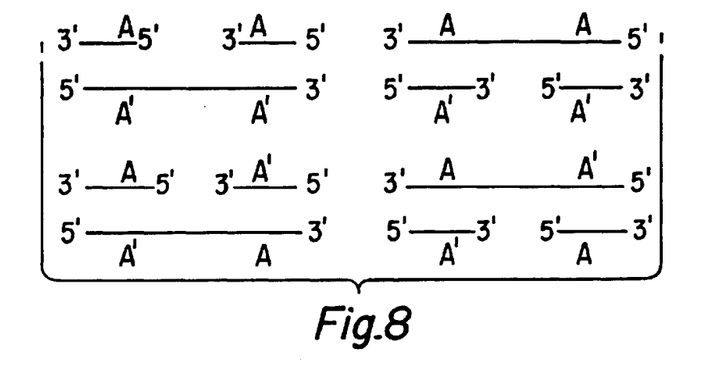
FIG. 8 shows a schematic representation of four examples of a 200 bp DNA duplex having a single nick.
Figure 9:
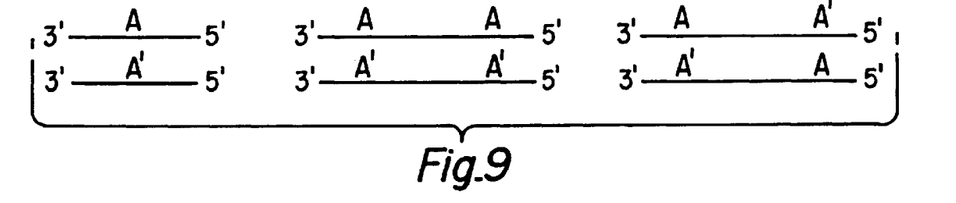
FIG. 9 shows a schematic representation of single stranded DNA fragments resulting from the denaturation of a 200 bp duplex having a single nick.

FIG. 3, a MIPC separation at 80° C., of the isolated 100 bp ladder component shows two peaks, indicating that the 100 bp fragment was not nicked. However, the putative nicked 200 bp fragment, which was isolated and re-chromatographed by MIPC at 80° C., shows five peaks representing six fragments as shown in FIG. 4. This result indicates the presence of one nick. The reason six fragments are formed upon denaturation of a 200 bp ladder fragment is because the fragment is constructed by enzymatic ligation of 100 bp base pair fragments. The 100 base pair fragment is composed of polynucleotide strand A and its complimentary strand A' as shown in FIG. 6. Ligation can form two, 200 bp dsDNA fragments having different sequences, i.e., A—A/A'—A' and A–A'/A'–A as shown in FIG. 7. If incomplete ligation results, then the four fragments shown in FIG. 8 will be formed. FIG. 9 shows the six single strands which will be produced upon denaturation, if incomplete ligation occurs in a statistical fashion. The shortest single strands of 100 bp each, A and A' appear at the lowest retention time in FIG. 4, as expected. The three peaks between 10 and 11 minutes, represent the four 200 bp single strands. A–A' and A'–A co-elute, and the peak representing these fragments is, therefore, twice the area of the separated A—A and A–A' fragments.

Other fragments in the 100 bp ladder which appear homogenous in GEP separations, show similar nicks in one or more locations when analyzed by MIPC. Ladders with nicks cannot be used as base pair length standards in MIPC because of the ambiguity created by the separated nicked strands. However, by treating the commercially obtained 100 bp ladder with ligase enzyme (e.g., T4 DNA ligase, Part No. 600011, Stratagene, La Jolla, Calif.; Pfu DNA ligase, a DNA ligase isolated from *Pyrococcus furiosus* and available as Product No. 600191 from Stratagene, and further described in U.S. Pat. No. 5,506,137; DNA ligase, Part No. 15628-019, Life Technologies, Inc.; DNA ligase from *Thermus thermophilus*, as described by Takahashi, et al., *J. Biol. Chem.* 259:10041 (1984)), the nicks will be repaired. Alternatively, a commercial source which provides 100 bp ladders without nicked fragments (Life Technologies, Inc.) can be used. In either case, when an un-nicked 100 bp ladder is chromatographed on a MIPC column, a base pair length standard chromatogram is created and can be stored in computer memory for later recall and comparison with a sample to ascertain the base pair lengths of DNA fragments therein. The column is thus calibrated for base pair length. Such a standard chromatogram is shown in FIG. 5. The upper five chromatograms were obtained using a 100 bp ladder from Life Technologies, Inc. The chromatograms are offset by 5 millivolts. The lower two chromatograms were obtained using a standard pUC18 HaeIII restriction enzyme digest containing DNA fragments having base pair lengths of 80, 102, 174, 257, 267, 298, 434, 458 and 587. The samples were applied to an MIPC column at non-denaturing temperature, 50° C. The column was eluted with a mobile phase linear gradient comprising Solvent A (0.1M TEM, pH 7) and Solvent B (0.1M TEAA in 25% acetonitrile). The flow rate was 0.90 mL/min and detection was by UV at 260 nm. The separation column was 50×4.6 mm i.d. and contained octadecyl modified, nonporous poly (ethylvinylbenzene-divinylbenzene) beads (DNASEP, Transgenomic, Inc.). The gradient is shown below:

| Time (min.) | % A | % B |
| --- | --- | --- |
| 0.0 | 91 | 9 |
| 5.2 | 88 | 12 |
| 7.2 | 85 | 15 |
| 9.2 | 84 | 16 |
| 14.2 | 83 | 17 |
| 14.3 | 75 | 25 |
| 14.8 | 75 | 25 |
| 14.9 | 91 | 9 |
| 16.9 | 91 | 9 |

Calibrated MIPC columns can also be used in the present invention to determine the mobile phase composition required to elute a fragment whose base pair length is known or has been determined from the standard ladder chromatogram. This is done by determining, from the MIPC chromatogram, the compositions of the mobile phase gradient at the retention times of the fragments in a DNA ladder or restriction digest, whose base pair length is known. A relationship is then derived relating base pair length to mobile phase composition. Such a relationship is most conveniently expressed in the form of a reference curve wherein the base pair length is plotted on one axis and the retention time is plotted on the other axis. This methodology is very useful since it expedites methods development time required for the analysis of samples having a known base pair length. Conversely, the base pair length of an unknown fragment can be determined by comparing the mobile phase concentration at the observed retention time of the unknown fragment to the base pair length on the reference curve which corresponds to that mobile phase concentration.

Figure 11:
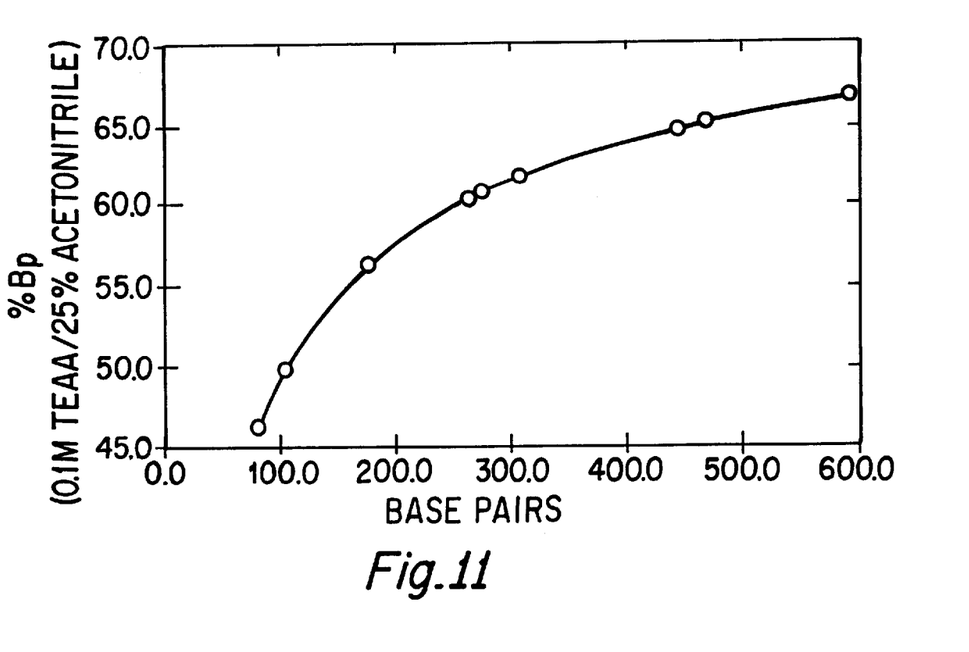
FIG. 11 is a reference chart showing percent B in the mobile phase vs. base pair length.

As an example, the reference relating the organic solvent concentration in the mobile phase required to elute DNA fragments having different base pair lengths is represented by the graph in FIG. 11. It is to be understood that the relationship depicted in the graph in FIG. 11 can be expressed over different ranges of base pair length and solvent concentrations. The data used to generate the reference depicted in FIG. 11 can be represented as a graph or a table. The data can be used to obtain an equation of a best-fit curve. For example, the following equation gave the curve shown in FIG. 11 (where buffer B contained 0.1 M TEAA, 25% acetonitrile and buffer A contained 0.1 M TEAA):

% $B_p = 19.24 + [53.6 \cdot bp/(78.5 + bp)]$

The reference graph, FIG. 11, was derived by Applicants as described in Example 3. Standard fragments of known base pair lengths were applied to an MIPC column and the concentration of organic solvent in the mobile phase sufficient to elute each fragment was determined when the chromatography was conducted at 50° C. The concentrations of organic solvent so determined, were plotted against their respective base pair length fragments to create FIG. 11. The standard fragments of known base pair length were obtained from a pUC18 DNA-HaeIII digest (S6293, Sigma-Aldrich). It is to be understood that the method described herein for creating the reference of FIG. 11 is only one of many other methods which can be used to construct such a reference. For example, other sets of standard fragments, such as ladders, could be used.

The essential, and heretofore unrecognized feature of the invention on which the reference concept is based, is the discovery by Applicants that under non-denaturing conditions, DNA fragments are separated by their size and this separation is highly reproducible using MIPC. Therefore, it is not necessary to calibrate a MIPC column for each sample analysis. Daily or even weekly calibrations are usually not necessary. Once a solvent concentration has been determined for a given base pair length, the retention time of that fragment will be constant at that solvent concentration, not only from day to day on the same column, but also from one column to another. It is this surprising discovery that makes it possible to create a reference relating solvent concentration to base pair length and to predict a preliminary solvent concentration for eluting a DNA fragment of known base pair length without any additional methods development. Although good results can be obtained with default values and no calibration, preferred practice is to calibrate when a new column or eluant (buffer or mobile phase) is installed on the instrument.

Another embodiment of the present invention is the use of DNA ladders in MIPC to monitor column performance. Unlike GEP, which requires a calibration standard for each run, MIPC columns do not require regular calibration; a time consuming process. However, over many injections, a MIPC column may begin to lose its separation efficiency. The separation efficiency of an MIPC column can be monitored by injecting a DNA ladder and noting the resolution and retention times of the fragments therein, compared to their resolution and retention times when the column was new. Any significant change in resolution and/or retention time indicates that the column is losing its separation efficiency. The separation efficiency of an MIPC column can be restored by washing the column, e.g., with mobile phase containing 0.1M EDTA at 80° C. Column separation efficiency is monitored using a standard DNA ladder after every 1,000 injections and preferably after every 500 injections.

In another aspect, the quality of a commercially obtained DNA ladder can be ensured for use with an MIPC column by treating the ladder with a ligase enzyme in order to seal any nicks which may be present therein. Although the use of ligase enzymes is well known (Pritchard, et al., *Nucleic Acids Research* 25:3403 (1997)), the present approach which uses MIPC to ensure the quality of commercially available DNA ladders has not been previously reported.

Although the above discussion focussed on the use of DNA ladders to provide standard reference MIPC chromatograms which could be used to relate retention time and base pair length, any mixture which contains a range of known base pair length fragments can be used for this purpose. For example, a restriction enzyme digest which produces fragments of known length can be separated on an MIPC column and the resulting chromatogram can serve as a reference chromatogram relating base pair length and retention time. A puc18 DNA-HaeIII restriction digest is shown in the two lowest traces of FIG. 5.

Another embodiment of the present invention is a method for determining the presence of nicks in a dsDNA fragment. In this embodiment, a dsDNA fragment is analyzed on a MIPC column under non-denaturing conditions, i.e., about 50° C., to produce a first chromatogram indicating the presence of n dsDNA species. The same fragment is then analyzed by MIPC under completely denaturing conditions, i.e., about 80° C. to provide a second chromatogram. The second chromatogram is then compared to the first chromatogram. If the second chromatogram indicates the presence of more than 2n single stranded DNA species, then the fragment contains at least one nick. To determine the actual number of nicks in a fragment, the source of the fragment must be known. Thus, a DNA fragment prepared by homo-ligation of smaller fragments of equal base pair length using a ligase (e.g., as in the preparation of a DNA ladder) will produce a number of fragments based on the statistical combination of ligated and nicked fragments as discussed in detail above. A fragment in which a nick which was produced by an enzyme which recognizes and nicks base pair mismatches in a heteroduplex, for example, will produce n+2 fragments, where n is the number of nicks in the fragment.

Mutations often are produced in PCR amplifications as a result of imperfect replication of a template. This can cause ambiguity in determining whether a mutation detected in a sample which has been amplified by PCR is real, or if it was produced during PCR amplification. Imperfect replication during PCR is a phenomenon recognized and thoroughly addressed by Applicants in co-pending U.S. patent applications cited hereinabove. The present invention can be used to optimize PCR processes by analyzing PCR reactions for PCR-induced mutations and adjusting reaction conditions (e.g., the source of DNA polymerase, dNTP concentrations, $Mg^{++}$ concentration, or temperature cycling conditions) for best results.

Figure 10:
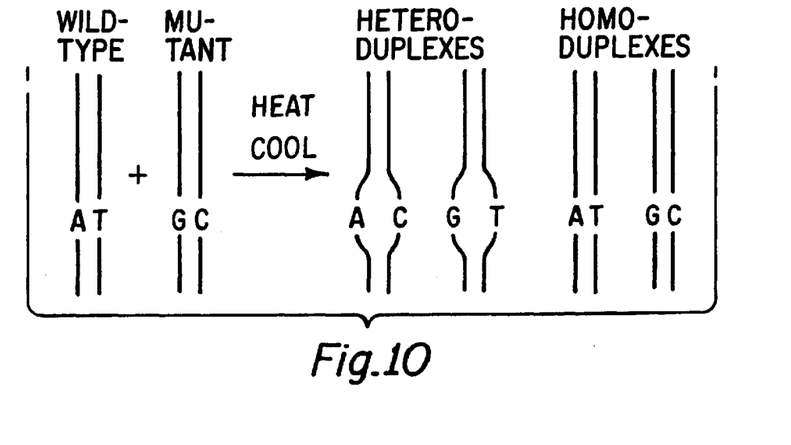
FIG. 10 shows a schematic representation of a hybridization to form homoduplex and heteroduplex.

In still another embodiment, the present invention provides an improved chromatographic method for determining the presence of one or more mutations in DNA samples. The method comprises hybridizing a sample containing a putative mutation with a corresponding wild type DNA fragment to produce a mixture of homoduplexes and heteroduplexes if the sample contains a mutation. If the sample does not contain a mutation, then only wild type homoduplexes will be produced as a result of the hybridization process. Hybridization, shown schematically in FIG. 10, is accomplished by heating a sample and its corresponding wild type to about 90° C. at which temperature the dsDNA is completely denatured. Upon slow cooling to ambient temperature over about a one hour period, the denatured polynucleotide strands recombine to form duplexes based on a statistical recombination of all the single strands present in the mixture. Denaturing is frequently effected by heat, but DNA strands can also be denatured for use in this invention, other methods non-limiting examples of which include pH, ionic strength, and chemical reagents such as urea and dimethylformamide.

The hybridized mixture is then contacted with a mutation site recognition agent which can recognize a mutation site (a base pair mismatch) and cleave one strand of a heteroduplex at the site of base pair mismatch to produce a "nicked" duplex.

Following treatment with the mutation site recognition agent as described above, the sample is analyzed using MIPC. Although MIPC separates DNA fragments on the basis of size rather than base pair sequence, fragments having the same base pair length can be separated if there is a significant alteration to the DNA fragment structure which would modify its polarity, such as a nick. Thus, in one embodiment of the invention, a DNA fragment is analyzed once using MIPC under nondenaturing conditions and then analyzed again after treatment with a site recognition agent. Nicked mutation containing duplexes separate from their unnicked counterparts even though they have the same base pair length. However, in order to unambiguously determine the presence of a mutation after contacting the sample with a nicking enzyme or chemical reagent, the MIPC analysis is performed under fully denaturing conditions, i.e., at a temperature which is sufficient to completely denature all the duplexes in the hybridized sample, both with and without pretreatment with the site recognition agent. If a mutation is present, the number of fragments seen after treatment will be increased. The contiguous strand of the duplex will produce one single strand, while the nicked strand (formed if a mutation were present) will produce at least two shorter single strands, depending on the number of nicks in the strand. Because the sizes of these denatured single strands will generally all be different, MIPC will separate and detect the total number of single strands in the sample following treatment with a mutation site recognition agent. The total number of single strands is related to the number of nicks in the heteroduplex and, therefore, to the number of mutation sites in the sample. This relationship can be expressed by the formula, $Nm=Ns-2$, wherein $Nm$ is the number of mutation sites in a heteroduplex strand and $Ns$ is the number of single strands produced and detected by MIPC under fully denaturing conditions.

In an important aspect, the present invention provides a method for mutation detection in a dsDNA sample. In a preferred embodiment of the method, a portion of the sample is chromatographed using MIPC under denaturing conditions, prior to being contacted with a mutation site recognition agent, to produce a first chromatogram. The first chromatogram, which serves as a reference, will produce two peaks having equal areas. These peaks represent the denatured complimentary single strands of the sample. Another aliquot of the sample is then hybridized with wild type and contacted with a mutation site nicking reagent to produce a product. The product is chromatographed under denaturing conditions using MIPC, to separate and detect the components therein and produce a second chromatogram. The second chromatogram is then compared to the reference chromatogram. An increase in the number peaks in the chromatogram of the sample after contact with the mutation site nicking reagent compared to the reference chromatogram, indicates the presence of, at least, one mutation site.

In one embodiment, the mutation site nicking reagent is an enzyme which nicks one strand of a heteroduplex within the vicinity of the site of base pair mismatch. Examples of such protein reagents include MutL, MutS, MutH, and exonuclease III of *E. coli* as described in U.S. Pat. No. 5,376,526 to Brown (1994), as well as S1 nuclease and mung bean endonuclease (Cotton, *Mutation Detection*, p 88, Oxford University Press (1997); Shenk, et al., *Cold Springs Harbor Symp. Quant. Biol.* 1:61 (1975)). Various DNA mismatch repair enzymes, mismatch repair enzymes, MutY protein, MutS protein, MutH protein, MutL protein, cleavase and HINF1, are also effective in recognizing and nicking sites of base pair mismatch in a heteroduplex as described in detail in the following references: U.S. Pat. No. 5,763,178 to Chirikjian (1998); and *Laboratory Methods for the Detection of Mutations and Polymorphisms in DNA*, G. R. Taylor ed., CRC Press, New York, pp. 195–205 (1997). A preferred enzyme reagent for use in the method of the present invention is a plant-derived nuclease called CEL 1 which is specific for DNA distortions and mismatches as described by Oleykowski et al., *Nucleic Acids Res.* 26:4597 (1998). These three reference and the references contained therein are hereby incorporated in their entireties herein. It will be appreciated that these references fully describe methods for isolation of these enzymes, the conditions for their use, and product analysis using gel electrophoresis and autoradiography. The present invention, however, is directed to the analysis of the reaction products using MIPC as the preferred separation method.

In still another aspect of this invention, homozygous mutations, i.e. homoduplexes having a base pair sequence which differs from wild type by at least one base pair can be detected. The sequence of the wild type and the position of a putative mutation site must be known, as is the case in most screening applications. In this embodiment, a putative homozygous mutation is denatured and two polynucleotide strands, each shorter than the denatured mutation strand, are added. One strand is complimentary to the denatured putative mutant strand from the mutation site towards the 3'-end. The other strand is complimentary to the denatured putative mutant strand from the mutation site towards the 5'-end. Upon recombination, the two short strands will anneal to the putative mutant strand, but leave a nick at the putative mutation site. A ligase enzyme is then added to repair the nick. However, since the wild type sequence is known, only the dNTP which is complimentary to wild type at that position is added. Under this condition, only the nick in a wild type sample will be sealed by a ligase. If the sample contained a mutation, the ligase will not seal the mutation site, since the dNTP which is complimentary to the mutant base was not present in the ligase reaction mixture. Analysis of such a ligase treated sample by MIPC under fully denaturing conditions as described hereinabove, will reveal the presence or absence of a mutation by the number of fragments represented in the chromatogram. Preferred ligases for use in this embodiment include ligases such as *Thermus thermophilus* DNA ligase, T4 DNA ligase or T7DNA ligase are described by Pritchard, et al. in *Nucleic Acids Research* 25:3403 (1997) which is incorporated by reference in its entirety herein.

Although any chromatographic method, including MIPC, size exclusion chromatography, ion exchange chromatography, or reverse phase chromatography, can be used in the method of the present invention, the preferred chromatographic step comprises MIPC. Separations based on gel electrophoresis are excluded from the definition of chromatography as used herein.

An important aspect of the invention, surprisingly discovered by the Applicants, is that samples which have been treated with mutation site nicking enzymes such as those described herein can be analyzed directly by MIPC. It is not necessary to remove any endogenous reagents or by-products prior to analysis. This is unusual, since such endogenous material, especially proteins, usually interfere in HPLC separations. This discovery makes possible the unattended, automated analysis of multiple samples in mutation detection screening assays.

In another embodiment, the method of the invention can also be practiced by employing a non-proteinaceous chemical as a mutation site nicking reagent which will recognize and nick a single strand of a heteroduplex at the site of base pair mismatch. Such reagents include chemical intercalators which recognize a base sequence and upon activation, nick a single strand of a heteroduplex at the site of base pair mismatch. Such compounds are exemplified by organometallic substances, generally containing rhodium, ruthenium or cobalt. Activation of the intercalator to effect nicking is achieved by exposure of the intercalated complex to light having a suitable wave length, e.g., the 365 nm wavelength produced by a mercury/xenon arc lamp. Non limiting examples of such compounds include bis(2,2'-bipyridyl) chrysenequinone diimine rhodium(III), bis(2,2'-bipyridyl) chrysenequinone diimine rhodium(III), (2,2'-bipyridyl)-bis (phenanthrenequinone) diimine rhodium(III), (bis (phenanthroline)dipyridophenazine ruthenium(II), bis (phenanthroline)dipyridophenazine ruthenium(III). The syntheses and mutation detection properties of site selective organometallic intercalators is described by Barton, et al. in the following references: *J. Am Chem. Soc.* 119:12986 (1997); *J. Am. Chem. Soc.* 119:2921 (1997); *Inorg. Chem.* 37:29 (1998). These references and the references therein are herein incorporated in their entireties.

A referred reagent for use in the present invention is bis(2,2'-bipyridyl) chrysenequinone diimine rhodium(III). The synthesis and mutation detection properties of this compound are described by Jackson, et al. (*J. Am. Chem. Soc.* 119:12986 (1997). This reference and the references contained therein are incorporated in their entireties herein. It is thought that site selective, non-covalent intercalation occurs because of helix destabilization caused by base pair mismatch in a heteroduplex. Mismatch recognition seems to be broadly correlated with the degree of helix destabilization caused by the mismatch which allows the bulky chrysene intercalator to bind. Photo-cleavage or nicking can be effected by irradiating the intercalated complex at 365 nm with a mercury/xenon arc lamp. Jackson and Barton have found that chrysene-rhodium(III) intercalator recognizes CC, CA, TT, TA, AA, and TC mismatches as evidenced by cleavage of at least one strand at or near these sites upon irradiation of the DNA chrysene-rhodium(III) complex at 365 nm.

An important aspect of the invention, surprisingly discovered by Applicants, is that samples which have been treated with sequence recognition organometallic intercalators can be analyzed directly by MIPC. It is not necessary to remove any endogenous reagents or by-products prior to analysis. This is unusual, since endogenous material such as organometallic compounds usually interfere in HPLC separations. This discovery makes possible the unattended, automated analysis of multiple samples in mutation detection screening assays.

It has been reported that enzymes such as S1 nuclease and other mutation site nicking reagents can cause non-specific cleavage of DNA. Such non-specific cleavage can create ambiguity in the analysis of a sample containing a putative mutation. In a preferred embodiment of the invention, therefore, a sample is analyzed after contact with an enzyme or other agent using MIPC at various time intervals. Such intervals can be 0, 2, 5, 7, 10, 15, 20, 25, 30, 40, 50, and 60 minutes. Since non-specific cleavage is generally much slower than specific cleavage, an analysis time can be determined at which the ratio of specific to non-specific cleavage is at a maximum. The sampling time so determined can then be used in subsequent screening.

Other features of the invention will become apparent in the course of the following descriptions of exemplary embodiments which are given for illustration of the invention and are not intended to be limiting thereof.

Procedures described in the past tense in the examples below have been carried out in the laboratory. Procedures described in the present tense have not yet been carried out in the laboratory, and are constructively reduced to practice with the filing of this application.

EXAMPLE 1

Detection of Nicked DNA by MIPC

Figure 2:
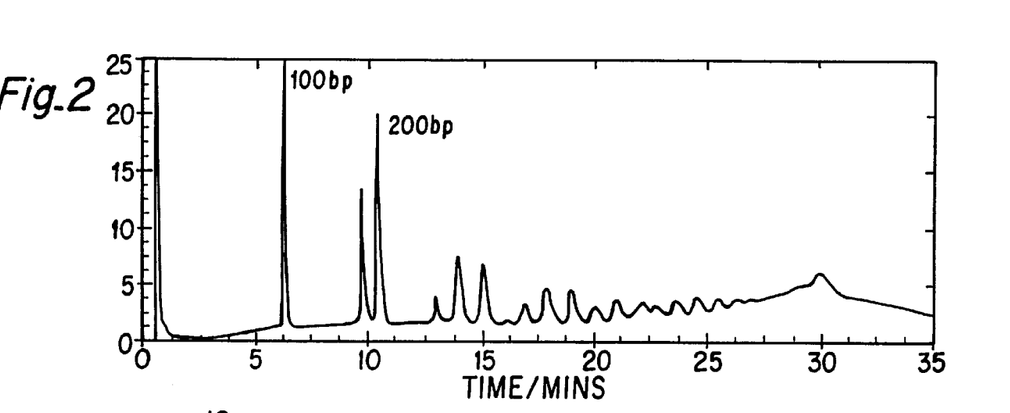
FIG. 2 is an MIPC chromatogram of a commercial 100 bp DNA ladder separated under non-denaturing conditions.

A commercial 100 bp dsDNA ladder (170-8206, BioRad) comprising base pair lengths 100 to 3,000 in 100 bp increments, was chromatographed on an MIPC column at 50° C. The column was eluted using the following gradient wherein solvent A was 0.1M triethyammonium acetate (TEM) and solvent B was 25% acetonitrile in 0.1M TEAA. The flow rate was 0.75 mL/min and UV detection was at 260 nm. The chromatogram is shown in FIG. 2.

| Time | % A | % B |
|------|-----|-----|
| 0–3  | 35  | 65  |
| 3    | 45  | 55  |
| 7    | 35  | 65  |
| 9.5  | 35  | 65  |
| 9.5  | 0   | 100 |
| 11   | 0   | 100 |
| 11   | 35  | 65  |

The 100 bp and 200 bp (peak 1) fragments (peak 3) each appeared as a sharp peak. However, a spurious peak, representing a nicked 200 bp fragment (peak 2), is seen between the 100 bp and 200 bp peaks.

The 100 bp, 200 bp, and spurious peak, separated as described above, were each collected and reanalyzed. The chromatography was repeated at 80° C., a temperature at which dsDNA would be completely denatured, all other conditions being identical. The 100 bp fragment, shown in FIG. 3, appeared as two sharp peaks representing the two denatured single strands A and complimentary A'. The 200 bp fragment, shown in FIG. 4, appeared as four peaks, representing the four possible single strands produced upon denaturing, A—A, A'—A', A–A', A'A. Each strand was a statistical combination of ligated 100 bp fragments. Spurious peak 2 was confirmed as being a 200 bp fragment having a single nick. The chromatogram of this material showed six peaks, A—A, A'—A', A–A', A'–A, A, and A', representing all the possible combinations of single strands which would be expected from such a material.

EXAMPLE 2

Calibration of an MIPC Column

A commercial dsDNA ladder was applied to an MIPC column. The column was eluted using a gradient of solvent A and solvent B as shown in the table below.

| Time | % A | % B |
|------|-----|-----|
| 0–3  | 35  | 65  |
| 3    | 45  | 55  |
| 7    | 35  | 65  |

-continued

| Time | % A | % B |
|---|---|---|
| 9.5 | 35 | 65 |
| 9.5 | 0 | 100 |
| 11 | 0 | 100 |
| 11 | 35 | 65 |

Solvent A was 0.1M triethyammonium acetate (TEM) and solvent B was 25% acetonitrile in 0.1M TEM. The flow rate was 0.75 mL/min and UV detection was at 260 nm.

The peaks and retention times of the separated base pair standards in the ladder are shown in FIG. 2.

EXAMPLE 3
Preparation of a Reference Graph of Mobile Phase vs. Nucleotide Base Pair Length A standard pUC18 HaeIII restriction enzyme digest containing DNA fragments having base pair lengths of 80, 102, 174, 257, 267, 298, 434, 458 and 587 was applied to an MIPC column at non-denaturing temperature, 50° C. The column was eluted with a mobile phase linear gradient comprising Solvent A (0.1M TEM, pH 7) and Solvent B (0.1M TEM in 25% acetonitrile). The flow rate was 0.75 ml/min and detection was by UV at 260 nm. The gradient is shown below:

| Time (min.) | % A | % B |
|---|---|---|
| 0.0 | 65 | 35 |
| 3.0 | 45 | 55 |
| 10.0 | 35 | 65 |
| 13.5 | 35 | 65 |
| 15.0 | 0 | 100 |
| 16.5 | 0 | 100 |
| 17.5 | 65 | 35 |
| 19 | 65 | 35 |

The reference curve (FIG. 11) was constructed by taking the retention time of each fragment and finding the corresponding % B from the gradient. The % B was then plotted against base pair as shown in FIG. 11.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

What is claimed is:

1. A method for determining the presence of a nick in a known fragment of double stranded DNA comprising:
   (a) applying said fragment to a Matched Ion Polynucleotide Chromatography column;
   (b) eluting said fragment under denaturing conditions;
   (c) detecting the single stranded DNA species eluted in step (b); and
   (d) quantifying the single stranded DNA species from step (c) wherein
      at least three single stranded DNA species are detected if said fragment has a nick.

2. A method of claim 1, wherein said denaturing conditions comprise an elevated level, sufficient for completely denaturing said fragment, of at least one of temperature, urea concentration, dimethylformamide concentration, organic solvent concentration, counterion concentration, and pH.

3. A method for determining the presence of a nick in a known fragment of double stranded DNA comprising:
   (a) applying said fragment to a reverse phase separation column;
   (b) eluting said fragment under denaturing conditions by Ion Pairing Reverse Phase HPLC;
   (c) detecting the single stranded DNA species eluted in step (b); and
   (d) quantifying the single stranded DNA species from step (c) wherein at
      least three single stranded DNA species are detected if said fragment has a nick.

4. A method of claim 3, wherein said denaturing conditions comprise an elevated level, sufficient for completely denaturing said fragment, of at least one of temperature, urea concentration, dimethyiformamide conoentration, organic solvent concentration, counterion concentration, and pH.

* * * * *